United States Patent [19]
Krumme

[11] Patent Number: 5,409,460
[45] Date of Patent: Apr. 25, 1995

[54] INTRA-LUMINAL EXPANDER ASSEMBLY

[75] Inventor: John F. Krumme, Tahoe City, Calif.

[73] Assignee: The Beta Group Inc., Menlo Park, Calif.

[21] Appl. No.: 48,352

[22] Filed: Apr. 15, 1993

[51] Int. Cl.⁶ .......................................... A61M 25/00
[52] U.S. Cl. .......................................................... 604/107
[58] Field of Search ............... 604/104, 105, 106, 281, 604/96, 107, 264, 280; 606/191, 194, 198; 128/772

[56] References Cited

U.S. PATENT DOCUMENTS

| | | | |
|---|---|---|---|
| 4,699,611 | 10/1987 | Bowden | 606/191 |
| 4,758,222 | 7/1988 | McCoy | 604/95 |
| 4,777,799 | 10/1988 | McCoy et al. | 60/528 |
| 4,790,624 | 12/1988 | Van Hoyl et al. | 350/96.26 |
| 4,808,163 | 2/1989 | Laub | 604/105 |
| 4,995,868 | 2/1991 | Brazier | 604/104 |
| 5,025,799 | 6/1991 | Wilson | 604/281 |
| 5,135,517 | 8/1992 | McCoy | 604/105 |
| 5,152,748 | 10/1992 | Chastagner | 604/95 |
| 5,215,103 | 6/1993 | Desai | 604/105 |
| 5,217,451 | 6/1993 | Fveitas | 604/105 |

Primary Examiner—C. Fred Rosenbaum
Assistant Examiner—Manuel Mendez
Attorney, Agent, or Firm—Stephen F. K. Yee

[57] ABSTRACT

An intra-luminal expander assembly for use with a catheter comprises an expandable tubular expander element having openings, for example slots, formed in it, and first and second fixation portions located at or towards its ends. The expander element is disposed around a core element which comprises a shape memory alloy which has been treated so that, when the temperature of the alloy is increased above its $A_s$ temperature, it displays a shape memory effect and the length of the core element decreases. The expander element is attached to the core element through the first fixation portion and oriented so that, as the length of the core element decreases when its temperature increases, the first fixation portion is caused to move relative to the second fixation portion in a direction towards the second fixation portion, and the second fixation portion being restrained against movement with the first fixation portion so that the length of the expander element decreases and its transverse dimension increases.

22 Claims, 3 Drawing Sheets

INTRA-LUMINAL EXPANDER ASSEMBLY

FIELD OF THE INVENTION

This invention relates to an intra-luminal expander assembly, and to a method of implanting an expander assembly in a lumen.

BACKGROUND TO THE INVENTION

A lumen in a human or animal body, such as a blood vessel or a urinary tract, can require internal support to ensure proper flow of fluid in the lumen. For example, a lumen can become at least partially occluded, and support can be required to reestablish sufficient internal bore in the lumen for flow of fluid.

Support for a lumen can be provided by implantation of a stent in the lumen. In many situations, this can allow a patient to resume normal activities without dependence on medical help, at least temporarily and in many situations indefinitely.

It can also be desirable to provide support in a lumen temporarily, without necessarily implanting a stent in the lumen. This can be achieved by means of a catheter which can be inserted into a lumen, and which has a portion which can be inflated by means of fluid supplied to the inflatable portion through a hollow bore of the catheter. This technique is referred to as "balloon angioplasty" when applied to blood vessels.

In processes in which inflatable catheters are used, the occlusion and the walls of the lumen are expanded and stretched by inflation of the catheter. The walls then remain in the stretched condition so as to remove or at least to reduce the occlusion, and to establish an increased flow of fluid in the lumen.

Once inflated, the catheter completely blocks the lumen against flow of liquid. The expansion process must therefore be carried out quickly, and then the catheter must be deflated quickly to reestablish flow of fluid. This is particularly critical in blood vessels on or near the heart which, if deprived of blood flow for even short periods (sometimes less than 30 seconds) can give rise to the condition known as "heart attack".

The present invention provides an expander assembly which includes a shape memory alloy component, which exhibits a shape memory effect. Shape memory alloys are discussed in an article by L. McDonald Schetky in the Encyclopedia of Chemical Technology (edited by Kirk-Othmer), volume 20, pages 726 to 736. Subject matter disclosed in that document is incorporated in this specification by this reference to the document. Such alloys can exist in martensite and austenite phases. An article formed from the alloy while in the austenite phase can be deformed, after it has been cooled so that the alloy is in the martensite phase. If the temperature of the article is subsequently increased so that the alloy transforms back to the austenite phase, the article reverts to the configuration which it had before it was deformed. The transformation from austenite phase to martensite phase takes place over the temperature range $M_s$ to $M_f$, and the transformation from martensite phase to austenite phase takes place over the temperature range $A_s$ to $A_f$.

SUMMARY OF THE INVENTION

The present invention provides an expander assembly in which a shape memory alloy component is used to cause an expander element with openings formed in it, positioned around the component, to expand transversely, in use to expand and to support a lumen in which the assembly is positioned.

In one aspect, the invention provides an intra-luminal expander assembly which comprises:
 (a) a tubular expander element having openings in it which allow it to be expanded transversely, and first and second fixation portions located at or towards opposite ends of the element, and
 (b) a core element comprising a shape memory alloy which has been treated so that, when the temperature of the alloy is increased above its $A_s$ temperature, it displays a shape memory effect and the length of the core element decreases, the core element extending through the expander element;
the expander element being attached to the core element through the first fixation portion and oriented so that, as the length of the core element decreases when its temperature increases, the first fixation portion is caused to move relative to the second fixation portion in a direction towards the second fixation portion, and the second fixation portion being restrained against movement relative to the first fixation portion so that the length of the expander element decreases and its transverse dimension increases.

The expander assembly of the invention has the advantage that materials of the expander element (which contacts the wall of the lumen) and the core element can be selected according to the requirements of the support required to be provided by the sheath and of the movement required to be imparted by the core. The material of the expander element can be selected to provide the appropriate physical support for the lumen. It can also be selected without restriction by any requirement for bio-compatibility during long term implantation, in contrast with stent assemblies in which the stent is formed from a shape memory alloy.

Furthermore, the use of an expander element with openings formed in it allows fluid to flow along a lumen via the openings even when the expander element is located in the lumen and is expanding it. Problems arising from stopped flow of fluid, especially blood, when a balloon catheter is used are therefore avoided. The assembly of the present invention therefore allows the expansion to take place less hurriedly than in the case with an inflatable catheter. Slower expansion is considered likely also to give rise to the advantage of reduced damage to the tissue of the wall of the lumen.

A further advantage of the assembly of this invention is that, as a result of the openings in the expansion element which allow it to expand, and which allow fluid flow through it, the amount of material in the expansion element is reduced compared with a device with an intact wall arranged for inflation. This facilitates packaging of the assembly, and delivery to the location in the lumen where it is to be deployed.

The core element of the expander assembly may comprise a portion which is formed from a shape memory alloy which exhibits a shape memory effect and another portion. The two portions will generally be adjacent one another along the length of the core element. The portion which exhibits the shape memory effect will be configured to provide sufficient movement to cause the expander element of the assembly to change in configuration to support the lumen.

Generally, the length of the portion of the core element which exhibits a shape memory effect will be longer than the expander element before it has been deformed. Generally, at least a portion, and preferably all, of the core element within the expander element will exhibit the shape memory effect. More preferably, the portion of the core element which exhibits the shape memory effect extends from one of the fixation portions of the expander element to beyond the other of the fixation portions.

The portion of the core element which exhibits a shape memory effect preferably comprises an alloy based on a nickel-titanium alloy, optionally with other elements such as chromium, copper, iron and vanadium. An example of a particularly preferred alloy consists of 50.3% atomic per cent nickel and 49.7% atomic per cent titanium, which has been treated so that its transformation temperatures are approximately as follows (in °C):

$M_s$ 0
$M_f$ −10
$A_s$ 42
$A_f$ 48

Other shape memory alloys, such as those based on nickel-palladium or copper, may be used. When the core element comprises a portion which exhibits a shape memory effect and another portion, the other portion may comprise an alloy which exhibits pseudoelastic or superelastic properties. These properties of shape memory alloys are discussed in the Schetky article referred to above. The use of a pseudoelastic or superelastic alloy as a core in a catheter is disclosed in EP-A-141006. Subject matter disclosed in that document is disclosed in this specification by this reference to the document.

The expander assembly can include a sheath which surrounds the core element, to which the second fixation portion of the expander element is attached so that the sheath and the expander element are oriented contiguously with respect to one another along the core element. This is particularly preferred when the shape memory effect portion of the core element includes a portion which protrudes from the expander element. The provision of a sheath allows movement of the core element relative to the expander element, even when the shape memory effect portion of the core element is longer than the expander element.

The sheath is generally connected at or towards one end to the expander element. It can extend along substantially the entire length of the core element extending away from the expander element. Alternatively, it can extend along just a portion of the core element proximal to the expander element. In this case, the sheath can be connected to the core element, generally to a portion which does not exhibit a shape memory effect, for example by means of a mechanical connector (for example a crimped ferrule) or by means of a weld or solder joint.

Preferably, the sheath comprises a helically wound wire. This has the advantage of allowing the expander assembly to flex in the portion in which the sheath is present, which can be advantageous when the expander assembly is to be manoeuvred along a tortuous path through lumina, for example through blood vessels, to a desired location.

A connection between the expander element and the core element, and a sheath if present, is preferably made mechanically, for example by means of a crimped ferrule or by welding. For some applications, it can be preferred that the connection be breakable, so that the expander element can be left in situ in the lumen, while the core element is removed. This can be achieved, for example, using a dematable connection to the expander element, for example a screw-threaded connection or a bayonet connection, or a connection which can be released mechanically remotely.

Preferably, the expander assembly includes a collar formed from the deformable material, which is located around the openings in the expander element. The provision of a collar has the advantage that the configuration of the expander element, after it has expanded transversely, can be controlled: the expander element will tend to expand in regions in which the material from which it is made is weakest. A collar can reinforce the expander element in selected regions as desired. The thickness of the material of the collar can vary along the length of the collar, so that the support given to the expander element changes along the length of the expander element. Preferably, the collar is located around the portion of the expander element in which the openings are provided so that that portion protrudes from at least one end of the collar. This has significant advantages in that the sleeve can provide selective support for the expander element to control its configuration when expanded, while also allowing fluids to flow along the lumen after the expander assembly has been expanded, the fluids flowing along the lumen through the expander element, via the openings therein.

A further advantage of the use of a collar on the expander element is that it can encourage contraction of the expander element so that it can be released from the internal wall of the lumen for removal from the lumen.

Preferably, the collar is formed from a polymeric material. Examples of suitable materials include medical grade silicone, and polyurethane.

Preferably, the expander element is formed from a metal. The metal will be selected for properties which make it suitable for use in the desired application; for example, it will be bio-compatible. For some applications, it can be preferred for the metal to be selected with physical properties which allow it to be deformed by the core element so that it retains the deformed configuration and remains in it to support the lumen, without requiring any hold-out force by the core element. For example, the expander element may be deformed plastically by the core element as the length of the core element decreases.

The expander element can for some applications require the core element to remain within it to provide a hold-out force to retain the expander element in its expanded configuration. This can be employed to allow the expander assembly to be removed from a lumen. For example, the expander element can be arranged to be capable of (a) being deformed by the core element so that its transverse dimension increases when the alloy of the core element transforms from martensite phase to austenite phase, and (b) deforming the core element so that its length increases when the alloy of the core element transforms from austenite phase to martensite phase, when the transverse dimension of the expander element decreases. This can be achieved particularly conveniently when the $M_s$ temperature of the alloy of the core element is less than body temperature.

The expander element can be retained on the core element while it supports a lumen. The expander element can be used to deliver a stent, the stent being provided on the expander element to be expanded by the expander element as its transverse dimension increases. The expander element itself might be implanted in a lumen by the core element, to function as an implanted stent after the core element has been removed.

The expander element can be formed from a stainless steel with appropriate resilient characteristics, such as found in 316 series alloys. The expander element can be formed from a shape memory alloy which exhibits pseudoelastic or superelastic properties, or a combination of the two.

The expander element can be formed from a shape memory alloy, which displays the shape memory effect, or which exhibits pseudoelastic or superelastic properties. When the expander element displays the shape memory effect, it is preferred that the $A_s$ temperature of the alloy be higher than the temperature of a patient in whose body the element is to be applied. A stent assembly which includes a stent element formed from a shape memory alloy is disclosed in the application filed concurrently with this application, which bears the title "An intra-luminal stent assembly". Subject matter disclosed in that application is incorporated in this specification by this reference.

It can be preferred for the expander assembly to include means for connecting the core element to a source of electrical power, so that current flows through the shape memory alloy of the core element which displays the shape memory effect. Generally, the core element can be connected directly to one terminal of a power supply at a convenient point along the length of the core element, generally at or towards a proximal end thereof. Another terminal of the power supply can be connected to the core element at or towards a remote end thereof by means of a conductor which extends along the core element and is insulated therefrom. The temperature of the core element can then be caused to increase so that it exceeds the $A_s$ temperature of the alloy by supplying power to the shape memory effect portion of the core element.

The openings in the expander element can usefully be provided as slots which extend along at least a portion of its length, preferably approximately parallel to the longitudinal axis of the assembly. Other configurations of openings can be used, provided that they can accommodate sufficient transverse expansion of the expander element. For example, the openings might be provided as an array of slits, or of rhombuses so that the deformation of the expander element will then involve, to an approximation, bending of the arms which define the slits or the rhombuses.

Preferably, the core element includes means for coupling with a source of inductively coupled power. This method of triggering the shape memory effect simplifies the assembly of the invention, by eliminating any requirement to connect components of the assembly to a source of electrical power. For example, it may include materials which couple with an inductive power source, such as a coating of a magnetic material. Suitable materials include iron. In this way, heating of the core element can be initiated externally by means of an inductive heat source. The expander assembly of the invention can also include means for heating the shape memory effect portion of the core element inductively, or heating the surface of the expander element that contact the walls of the lumen. Effects of the application of heat include increasing the temperature of the tissue to be expanded, which can reduce restenosis.

The shape memory effect portion of the core element can be treated so that the $A_s$ temperature of the shape memory alloy is slightly below body temperature. In this way, a expander assembly can be inserted into a lumen while at a temperature below the $A_s$ temperature of the alloy, and the expander element can be caused to expand due to an increase in temperature of the core element when exposed to body temperature.

In another aspect, the invention provides a method of implanting an expander assembly in a lumen, which comprises:

(a) locating in the lumen an expander assembly comprising
   (i) an expandable tubular expander element having openings in it which allow it to be expanded transversely, and first and second fixation portions located at or towards opposite ends of the element, and
   (ii) a core element comprising a shape memory alloy which has been treated so that, when the temperature of the alloy is increased above its $A_s$ temperature, it displays a shape memory effect and the length of the core element decreases, the core element extending through the expander element; and (b) causing the temperature of the core element to increase above the $A_s$ temperature of the alloy so that the lengths of the core element and of the expander element are made to decrease, and the transverse dimension of the expander element is made to increase.

DESCRIPTION OF PREFERRED EMBODIMENTS

Figure 1:
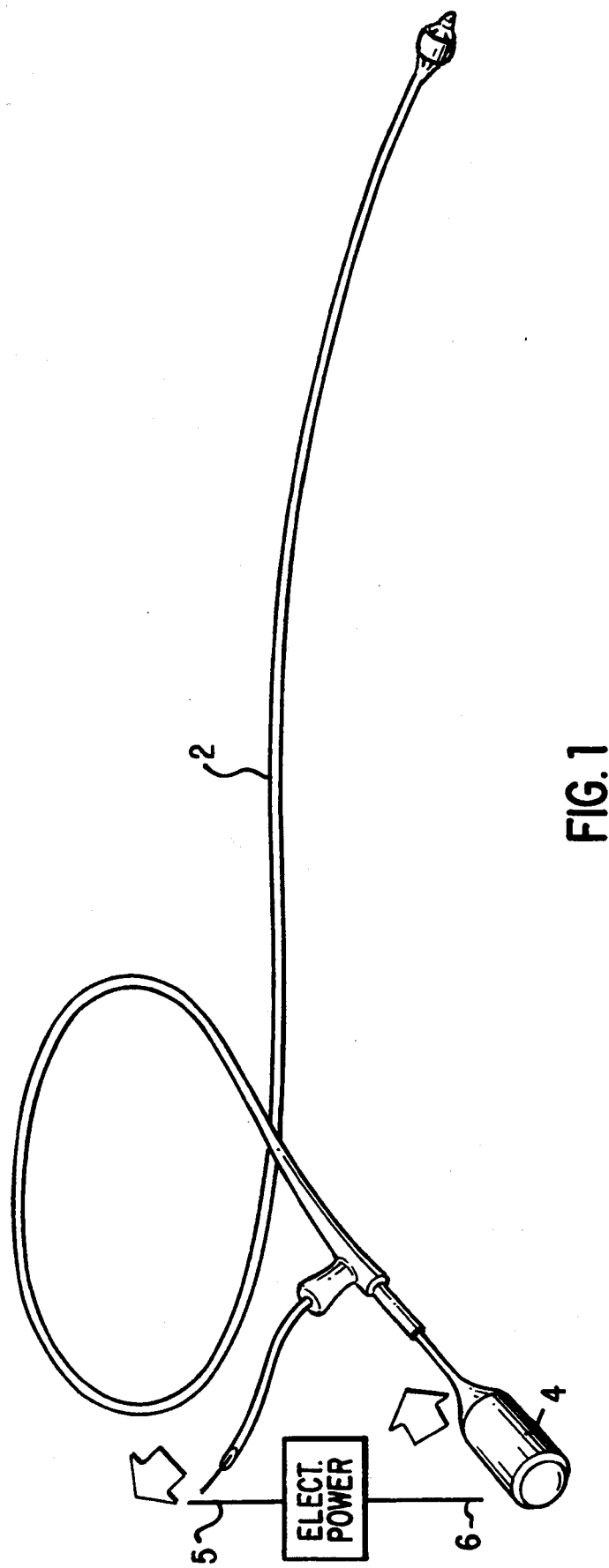
FIG. 1 is an isometric view of a expander assembly according to the invention.

FIG. 1 shows an expander assembly which includes a catheter by which an expander element can be delivered to a desired location in a lumen. The lumen may be, for example, a blood vessel such as a vein or an artery, or it may be a urinary tract. The expander element might be supplied to a blood vessel in the treatment of arteriosclerosis. The expander element might be supplied to the urethra in treatment of an enlarged prostate gland condition.

The expander assembly comprises an elongate catheter 2. The catheter comprises a core element and a sheath. The core element extends throughout the length of the catheter, and can be controlled rotationally at the distal end by means of a control element 4.

The core element comprises a shape memory alloy such as one based on a nickel-titanium alloy, optionally with one or more other elements. The distal end portion of the core element formed from the shape memory alloy is capable of exhibiting a shape memory effect. The length of the distal end portion of the core element can be reduced by heating the element so that its temperature exceeds the $A_s$ temperature of the alloy.

The portion of the core element other than the distal end portion is formed from a shape memory alloy which exhibits the property of optimised elasticity, which is referred to in U.S. Pat. Nos. 4,772,112 and 4,896,955. Subject matter disclosed in these documents is incorporated in this specification by this reference.

Terminals 5, 6 are provided as part of the catheter for connection of the core element to a supply of electrical power, so that current can be made to flow through the core element, or at least the distal end portion thereof.

Figure 2:
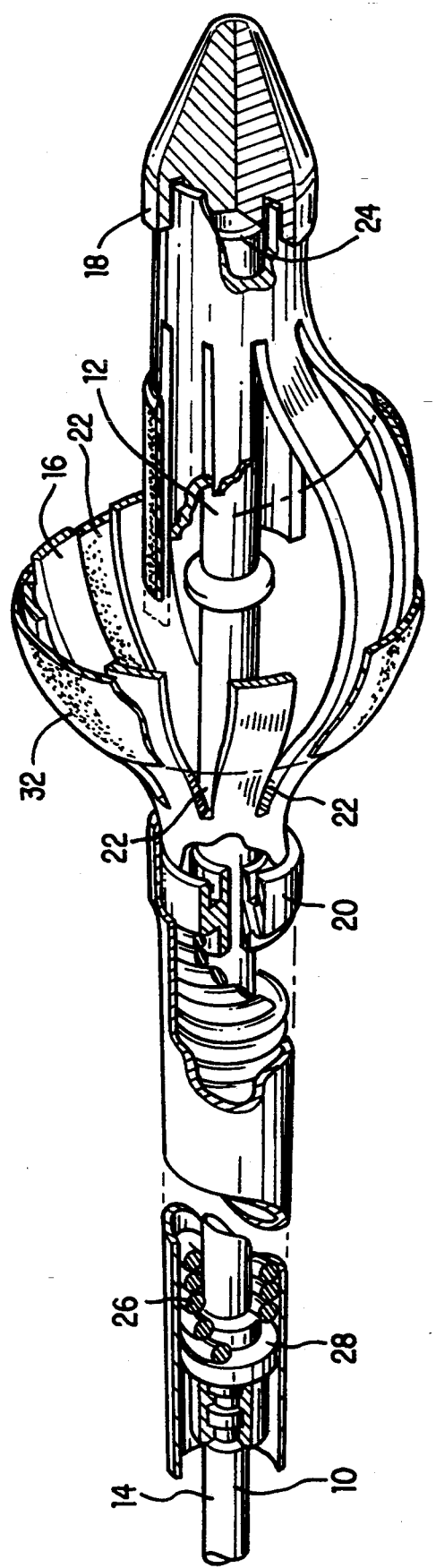
FIG. 2 is an isometric view of an end portion of the assembly shown in FIG. 1, partially cut-away.

FIG. 2 shows the distal end portion of the expander assembly. The core element 10 of the expander assembly comprises an end portion 12 formed from a shape memory alloy which exhibits a shape memory effect, and a proximal portion 14 to which the end portion is rigidly connected by means of a welded joint.

An expander element in the form of a slotted sleeve 16 is located around the end portion 12 of the core element. The expander element is formed from a stainless steel. The expander element is capable of being expanded radially outwardly, and of contracting elastically to or towards its original configuration.

The expander element has fixation portions 18, 20, at opposite ends of the slots 22. The expander element is connected to the end 24 of the core element by crimping.

The expander assembly includes a sheath 26 formed as a helically wound wire. The sheath is connected to the core element at about the junction between the end portion 12 and the proximal portion 14 of the core element 10. The connection is made by means of a ferrule 28. The core element is able to move within the sheath.

The second fixation portion 20 of the expander element 16 is connected to the sheath by means of a ferrule.

A collar 32 is located around the slotted portion of the expander element. The collar is located approximately centrally on the expander element, so that the slots 22 protrude from under the collar. The collar is formed from silicone polymer or a polyurethane.

The expander assembly is inserted into a lumen with the shape memory alloy of the end portion 12 of the core element in its martensite phase. The expander assembly is manoeuvred until the end portion of it, with the expander element 16 located where it is to be disposed, for example to support the wall of the lumen at the site of an occlusion. The temperature of the shape memory alloy of the end portion 12 of the core element is then caused to increase to a temperature above the $A_s$ of the alloy. This causes the length of the end portion of the core element to decrease. This causes the ends of the expander element to move relative to one another, towards one another, so that the length of the expander element decreases. This causes the transverse dimension of the expander element to increase, as the slots formed in it open.

The expander element 16 remains in its expanded configuration for as long as the shape memory alloy of the end portion 12 of the core element remains in the austenite phase. This will require power to be supplied continually to the core element for as long as the expander element is to remain expanded, unless the $M_s$ temperature of the alloy of the end portion is below body temperature. When the $M_s$ temperature of the alloy is below body temperature, disconnection of the core element from the source of electrical power can allow the expander element to contract radially, causing the length of the end portion of the core element to increase as it does so. This contraction can enable the expander assembly to be removed from the lumen.

Figure 3A:
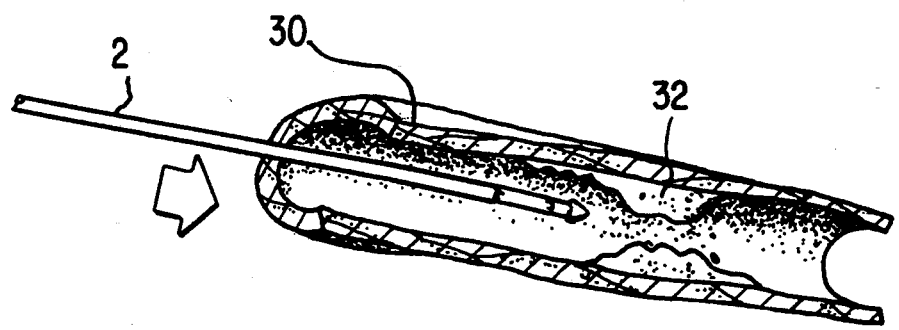
FIGS. 3A to 3C are illustrations showing how the assembly of the invention can be implanted in and removed from a lumen.
Figure 3B:
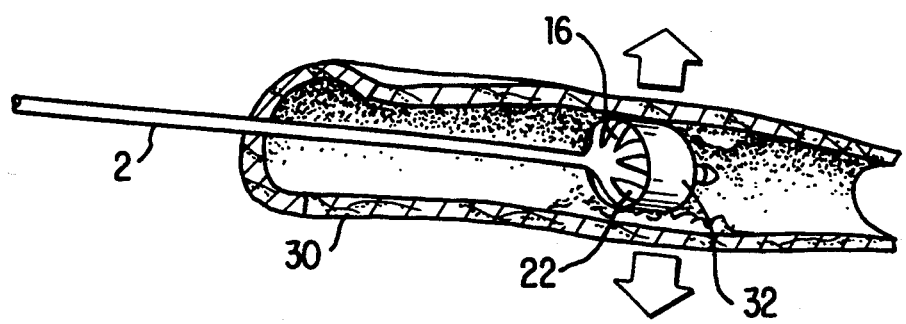
Figure 3C:
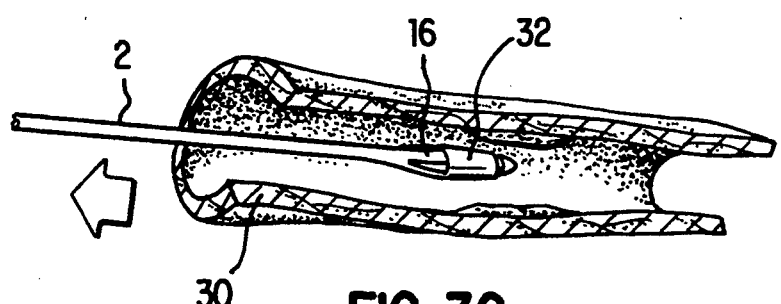

FIGS. 3A-3C show schematically how the expander assembly of the present invention can be used to widen a lumen 30 which is partially occluded by accumulated matter 32.

FIG. 3A shows the expander assembly being passed along the lumen so that the end portion thereof is located in the vicinity of the occlusion 32.

FIG. 3B shows the expander assembly while the expander element is expanded transversely, so that it is urged against the wall of the lumen, causing the occlusion 32 to be widened.

FIG. 3C shows the expander assembly after the expander element has contracted, so that it can be removed from the lumen.

What is claimed is:

1. An expander assembly for radially expanding a portion of a lumen, the assembly comprising:
   (a) a radially deformable tubular expander element having axially-extending openings formed in a defining wall which allow said expander element to be expanded radially, said expander element having first and second fixation portions located proximate opposite ends of the element, and
   (b) a core element comprising a shape memory alloy which has been treated so that, when the temperature of the alloy is increased above its $A_s$ temperature, it displays a shape memory effect and the length of the core element decreases;

the expander element encircling the core element and being maintained fixed longitudinally relative to the core element at the first and second fixation portions and disposed so that, with the expander assembly in place at a desired axial location along the lumen with the assembly axis oriented generally parallel to an axis of the lumen, as the length of the core element, between the first and second fixation portions, decreases when its temperature increases, the first fixation portion is caused to move relative to the second fixation portion in a direction towards the second fixation portion so that the axial dimension of the expander element decreases and its radial dimension increases.

2. An expander assembly as claimed in claim 1, in which the core element comprises at least two portions, of which one is formed from a shape memory alloy and displays a shape memory effect.

3. An expander assembly as claimed in claim 2, in which another of the portions of the core element is formed from a shape memory alloy, which exhibits the properties of superelasticity, or pseudoelasticity, or a combination thereof.

4. An expander assembly as claimed in claim 1, which includes a sheath which surrounds the core element, to which the second fixation portion of the expander element is attached so that the sheath and the expander element are oriented contiguously with respect to one another along the core element.

5. An expander assembly as claimed in claim 4, in which the sheath comprises a helically wound wire.

6. An expander assembly as claimed in claim 1, in which the filed longitudinal maintenance of the expander element at at least one of the fixation portions is made by means of a ferrule.

7. An expander assembly as claimed in claim 6, in which the expander element is formed from a stainless steel.

8. An expander assembly as claimed in claim 6, in which the expander element is formed from a shape memory alloy.

9. An expander assembly as claimed in claim 1, which includes a collar formed from a deformable material, which is located around the slits openings in the expander element.

10. An expander assembly as claimed in claim 9, in which the collar is formed of a polymeric material.

11. An expander assembly as claimed in claim 9, in which the thickness of the collar varies along the length of the collar.

12. An expander assembly as claimed in claim 1, in which the expander element is formed from a metal.

13. An expander assembly as claimed in claim 1, which includes means for connecting the core element to a source of electrical power, so that current flows through the shape memory alloy of the core element which displays the shape memory effect.

14. An expander assembly as claimed in claim 1, in which the openings are slits.

15. An expander assembly as claimed in claim 1, in which the openings are slots.

16. An expander assembly as claimed in claim 1, in which the openings are rhombic in shape.

17. An expander assembly as claimed in claim 1, in which the core element includes means for coupling with a source of inductively-coupled power to increase the temperature of the core element above its $A_s$ temperature.

18. An expander assembly as claimed in claim 17, in which the coupling means comprises a coating of a magnetic material which is responsive to an inductive heat source to increase the temperature of the core element.

19. An expander assembly as claimed in claim 1, which includes a stent element positioned around the expander element, so that the transverse dimension of the stent element increases with that of the expander element.

20. An expander assembly as claimed in claim 1, in which the fixed longitudinal maintenance of the expander element at at least one of the fixation portions is made by means of a separable connection so that the core element can be controllably separated from the expander element.

21. A method of implanting an expander assembly in a lumen to radially expand a portion of the lumen, which comprises:
   (a) introducing and locating at a desired position in the lumen an expander assembly comprising:
      (i) an expandable tubular expander element having axially extending openings formed in a defining wall which allow said expander element to be expanded transversely, and first and second fixation portions located proximate opposite ends of the element, and
      (ii) a core element comprising a shape memory alloy which has been treated so that, when the temperature of the alloy is increased above its $A_s$ temperature, it displays a shape memory effect and the length of the core element decrease, the expander element encircling the core element and being fixed longitudinally relative to the core element at the first and second fixation portions; and
   (b) causing the temperature of the core element to increase above the As temperature of the alloy so that the lengths of the core element and of the expander element are made to decrease, and the transverse dimension of the expander element is made to increase.

22. A method of radially expanding a portion of a lumen, comprising:
   (a) introducing and locating at a desired position in the lumen an expander assembly comprising:
      (i) an expandable tubular expander element having axially extending openings formed in a defining wall which allow said expander element to be expanded transversely, and first and second fixation portions located proximate opposite ends of the element, and
      (ii) a core element comprising a shape memory alloy which has been treated so that, when the temperature of the alloy is increased above its $A_s$ temperature, it displays a shape memory effect and the length of the core element decrease, the expander element encircling the core element and being fixed longitudinally relative to the core element at the first and second fixation portions;
   (b) causing the temperature of the core element to increase above the $A_s$ temperature of the alloy so that the lengths of the core element and of the expander element are made to decrease, and the transverse dimension of the expander element is made to increase, to radially expand the expander element and to radially expand the portion of the lumen where the expander assembly is positioned; and
   (c) permitting the temperature of the core element to decrease below the $A_s$ temperature of the alloy so that the lengths of the core element and the expander element are made to increase and the transverse dimension of the expander is made to decrease.

* * * * *

UNITED STATES PATENT AND TRADEMARK OFFICE
CERTIFICATE OF CORRECTION

PATENT NO. : 5,409,460

DATED : 25 April 1995

INVENTOR(S) : John F. KRUMME

It is certified that error appears in the above—identified patent and that said Letters Patent is hereby corrected as shown below:

Col. 1, line 60, change "$M_r$" to -- $M_f$ --

Col. 3, lines 17-20, spaces should appear between the temperature range and the temperatures, and the text should read as follows:

| | |
|---|---|
| $M_s$ | 0 |
| $M_f$ | -10 |
| $A_s$ | 42 |
| $A_f$ | 48 |

Col. 6, line 2, change "$A_s$temperature" to -- $A_s$ temperature --

Col. 6, line 6, change ".aspect" to -- aspect --

Col. 7, line 56, change "$M_s$temperature" to -- $M_s$ temperature --

Col. 8, line 58, change "the filed longitudinal" to -- the fixed longitudinal --

Col. 9, line 1, delete "slits"

UNITED STATES PATENT AND TRADEMARK OFFICE
CERTIFICATE OF CORRECTION

PATENT NO. : 5,409,460
DATED : April 25, 1995
INVENTOR(S) : John F. Krumme

It is certified that error appears in the above-indentified patent and that said Letters Patent is hereby corrected as shown below:

Col. 10, line 13, change "As" to -- $A_s$ --

Signed and Sealed this

Twenty-seventh Day of June, 1995

BRUCE LEHMAN

Attest:

Attesting Officer

Commissioner of Patents and Trademarks